United States Patent [19]

Bell et al.

[11] Patent Number: 4,533,643
[45] Date of Patent: Aug. 6, 1985

[54] METHOD FOR THE BATCH PREPARATION OF SAMPLE ALIQUOTS BY SOLVENT EXTRACTION AND SEPARATION OF SOLUBLES FROM NONSOLUBLE PARTICULATE

[75] Inventors: David R. Bell, Vernal, Utah; Theodore E. Miller, Jr., Midland, Mich.

[73] Assignee: The Dow Chemical Company, Midland, Mich.

[21] Appl. No.: 629,025

[22] Filed: Jul. 9, 1984

Related U.S. Application Data

[63] Continuation of Ser. No. 423,343, Sep. 24, 1982, abandoned, which is a continuation of Ser. No. 220,551, Dec. 29, 1980, abandoned.

[51] Int. Cl.$^3$ .............................................. G01N 1/10
[52] U.S. Cl. ................................ 436/178; 73/863.23; 73/863.83; 73/864.83; 422/68; 422/81; 422/101; 436/68; 436/85; 436/124; 436/177
[58] Field of Search ................... 436/68, 85, 124, 177, 436/178; 422/68, 78, 81, 101, 103; 73/863.23, 863.83, 863.81, 864.83

[56] References Cited

U.S. PATENT DOCUMENTS

| | | | |
|---|---|---|---|
| 3,249,403 | 5/1966 | Bochinski et al. | 73/864.83 |
| 3,790,347 | 2/1974 | Fletcher et al. | 422/78 |
| 4,148,610 | 4/1979 | Miller, Jr. et al. | 73/863.83 |

Primary Examiner—Michael S. Marcus
Attorney, Agent, or Firm—Burke M. Halldorson

[57] ABSTRACT

Method and apparatus for the batch preparation of sample aliquots by solvent extraction and separation of soluble species from sample comprising nonsoluble particulate, which comprises a receptacle which defines a sample receiving space into which a measured amount of sample is placed, a fluid-permeable filter which is remote from and communicates with the sample receiving space, means to add a metered quantity of solvent to the sample receiving space, means to supply pressurized gas to the sample receiving space to slurry the solvent with the sample, means to invert the receptacle to position the slurry into filtering contact with the filter, and means to collect a sample aliquot comprising the filtered liquid phase of the slurry.

3 Claims, 2 Drawing Figures

METHOD FOR THE BATCH PREPARATION OF SAMPLE ALIQUOTS BY SOLVENT EXTRACTION AND SEPARATION OF SOLUBLES FROM NONSOLUBLE PARTICULATE

This is a continuation of application Ser. No. 423,343 filed Sept. 24, 1982, which was a cont. of application Ser. No. 220,551, filed Dec. 29, 1980 each abandoned.

FIELD OF THE INVENTION

The invention relates broadly to method and apparatus for the batch preparation of sample aliquots, and more particularly, simple aliquots prepared by solvent extraction and separation of solubles of interest from nonsoluble particulate.

BACKGROUND OF THE INVENTION

Relevant prior art in the field of the invention is illustrated by the batch sample preparation technique described in U.S. Pat. No. 4,148,610. However, there is not any specific provision in this prior art technique for the extraction and separation functions required for the analysis of nonsoluble particulate samples. Thus, the technique as described specifically concerns the dissolution of samples in diluent apart from any extraction or separation of sample into soluble and nonsoluble components.

It is accordingly an objective of the invention to provide an automated method and apparatus suitable for the repetitive batch preparation of discrete sample aliquots by solvent extraction and separation of soluble species from nonsoluble particulate.

It is a further objective of the invention to provide such method and apparatus in which quantitative proportionality is achieved between the concentration of extracted components of interest in the sample aliquot and the concentration of same in the sample from which the extraction occurs.

It is yet another objective of the invention to provide such method and apparatus which are suitable for the preparation of sample aliquots, wherein respecting like samples, the dilution of sample in solvent is repetitively maintained at a fixed ratio.

BRIEF SUMMARY OF THE INVENTION

The invention as it relates to improved apparatus for the batch preparation of sample aliquots comprises a receptacle which defines a sample receiving space into which a measured amount of sample is placed, a fluid-permeable filter which is remote from and communicates with the sample receiving space, means to add a metered quantity of solvent to the sample receiving space, means to supply pressurized gas to the sample receiving space to slurry the solvent with the sample, means to invert the receptacle to position the slurry into filtering contact with the filter, and means to collect a sample aliquot comprising the filtered liquid phase of the slurry.

A further aspect of the invention relates to an improved method for the batch preparation of sample aliquots comprising: adding a batch quantity of sample containing nonsoluble particulate to a receptacle having a sample receiving space which communicates with a fluid permeable filter, the filter being disposed remote from the sample; adding a batch quantity of liquid solvent to the sample receiving space; injecting pressurized gas into the sample receiving space to slurry the solvent with the sample; inverting the receptacle to transfer the slurry into filtering contact with the filter; filtering the liquid phase of the slurry through the filter and collecting a metered amount of the filtered liquid phase to prepare a sample aliquot containing dissolved species extracted from the sample.

THE DRAWING

Yet further objectives, aspects and advantages of the invention will in part be pointed out in, and in part apparent from, the following more Detailed Description of the Invention considered together with the accompanying drawing wherein:

FIG. 1 is an elevational view illustrating a specific and preferred embodiment of apparatus constructed in accordance with the principles and teachings of the invention; and FIG. 2 is an enlarged cross-sectional view showing in greater detail certain of the components of the FIG. 1 apparatus.

DETAILED DESCRIPTION OF THE INVENTION

Figure 1:
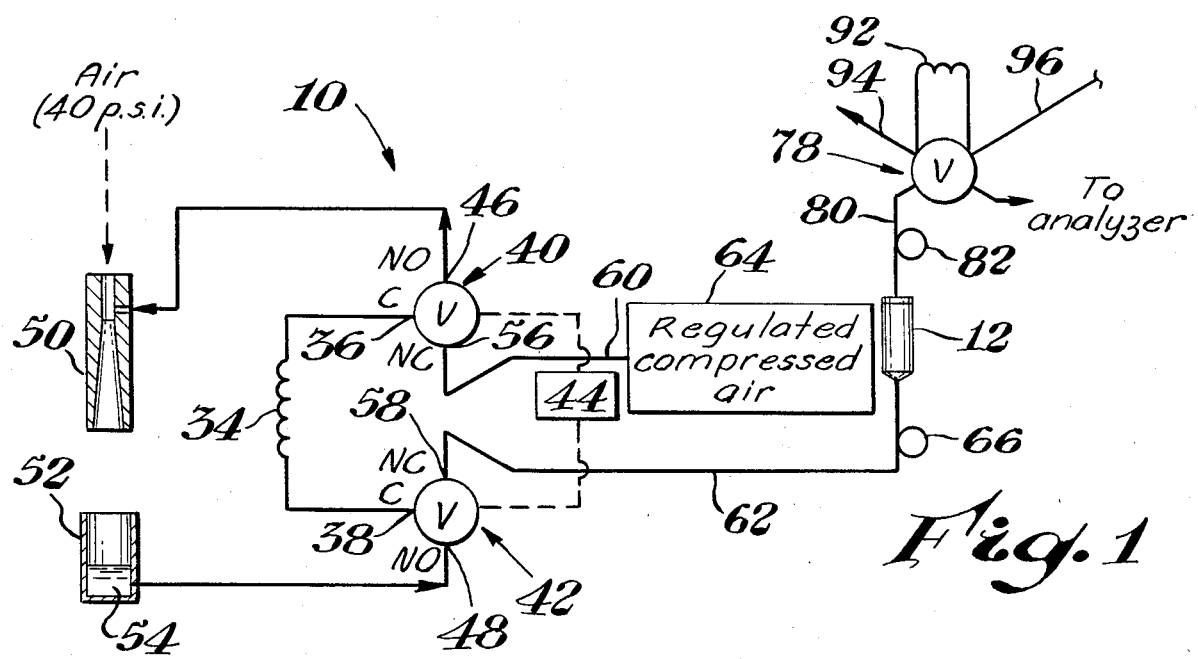
Figure 2:
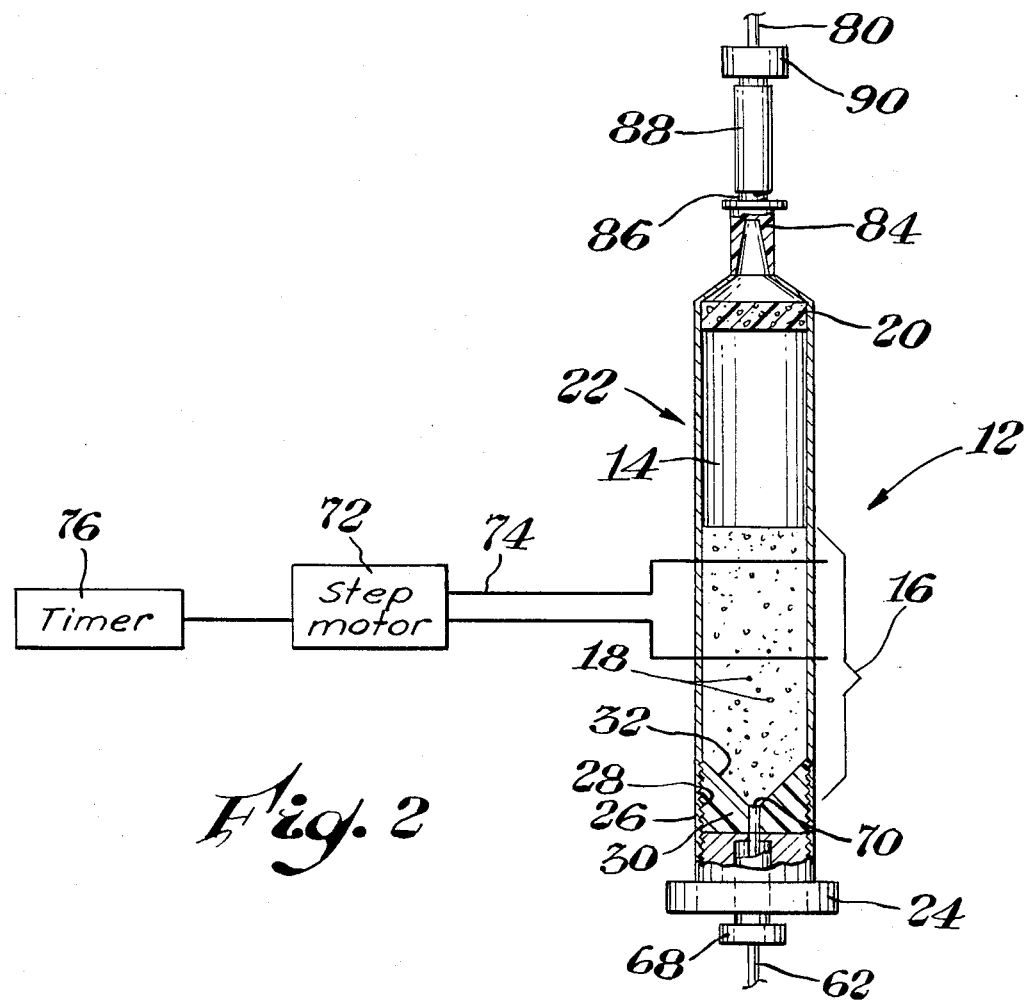

Referring to the drawing, there is illustrated in FIGS. 1 and 2, apparatus which is designed for the batch preparation of sample aliquots by solvent extraction and filtration of soluble species from sample comprising nonsoluble particulate.

The apparatus, designated generally by Reference Numeral 10, comprises a sample receptacle means 12 which defines a sample filtration chamber 14. The filtration chamber includes a sample receiving space or mixing chamber 16 into which a measured amount of particulate sample 18 is placed. A fluid permeable filter 20, which is impermeable to the nonsoluble particulate of sample 18, is disposed in filtration chamber 14 at a position remotely displaced from sample receiving space 16, and thus remotely displaced from the sample. Filter 20 is preferably constructed of a nonabsorbent material, e.g., a synthetic resinous plastic, to which is imparted permeable characteristics, e.g., by the formation of discretely sized pores or openings in the wall structure of the material.

A desired feature of the invention is the use of a disposable sample receptacle and filter which can be discarded after each use. To this end, the sample receptacle is, for the major part, preferably fabricated using the plastic cartridge or cartridge portion 22 of a standard laboratory syringe to which is added a disc filter 20 adapted to be discarded along with the cartridge.

Means for adding a batch quantity of particulate sample 18 to receptacle 12 preferably comprises a reusable plug 24 which is removably attached to cartridge 22, e.g., by clamping or by using a threaded plug 24 and tapping the lower end portion 26 of the cartridge as shown by threads 28. Plug 24, in the embodiment illustrated, is hollow and filled, e.g., with a slurry of an epoxy resin and aluminum powder which is cured to form a hardened machinable fill material 30 which can be drilled to define a generally conical depression 32. Depression 32 is a desirable configuration to assist complete wetting of the particulate sample with solvent to form a slurry mixture, as will be described more fully hereinafter.

Metered solvent addition means to add a batch quantity of liquid solvent to the filtration chamber comprises a metering loop or tube 34. The metering loop is connected between common ports 36, 38 of dual 3-way valves 40, 42, which are actuated commonly, e.g., by a solenoid controlled pneumatic actuator 44. Normally open ports 46, 48 of valves 40, 42, in turn, are connected respectively to an aspirator 50 and reservoir 52 containing liquid solvent 54. Normally closed ports 56, 58 of valves 40, 42, connect respectively to first and second conduits 60, 62, which communicate (by way of metering loop 34) between filtration chamber 14 and a regulated compressed gas cylinder or gas supply means 64. Second conduit 62, which is flexible as shown by looped portion 66, is connected to plug 24 by a threaded end fitting 68. Conduit 62 communicates with a central gas and solvent inlet port 70 defined by plug 24, and which is centered on the axis of conical depression 32.

Means to invert the sample receptacle comprises a motor 72, e.g., an electric step motor, the shaft of which is detachably connected to cartridge 22 such as by means of a ring-stand clamp 74. Motor 72 is operated preferably by a cam timer 76 to controllably orientate the sample receptable between alternately assumed noninverted and inverted positions. The noninverted position is defined by that orientation of filtration chamber 14 which places sample 18 in the sample receiving space (the position illustrated in FIG. 2). The inverted position of the sample receptacle is that position in which the filtration chamber is inverted to displace sample 18 into filtering contact with the remotely positioned filter 20.

Means to collect a sample aliquot, prepared by filtration through filter 20, comprises, e.g., an automatic sample valve 78 which communicates with the filtration chamber through a conduit 80 which, as indicated by looped portion 82, is flexible to allow for rotational movement. In the disposable cartridge 22 form of sample receptacle, removal of the needle assembly from the commercially supplied syringe (in adapting the latter to the invention) provides a raised nipple 84 to which conduit 80 may be detachably fastened, such as by means of a fitting 86 attached to nipple 84. Fitting 86, in turn, is joined to a threaded adaptor 88, and through adaptor 88, to an end fitting 90, which is joined to the end of conduit 80.

Sample valve 78 comprises a metering loop or tube 92 (indicated schematically). The contents of metering loop 92 are dispensed either to a sample drain conduit 94, or (depending on the position of valve 78) to an on-line analytical instrument through a conduit 96 adapted to contain a flowing carrier fluid. Alternatively, the sample aliquot may be collected and analyzed at a separate location, rather than directly on-line.

Operation

To operate apparatus 10, a weighed amount of sample is placed in a clean, disposable cartridge 22, containing a filter 20, and the cartridge is connected to the apparatus. Aspirator 50 is then activated, whereby solvent is drawn by the aspirator through metering loop 34 to fill it (any unused portion of the solvent being returned through the venturi passage of aspirator 50 to the reservoir). After filling of the metering loop, pneumatic actuator 44 actuates valves 40, 42 so that compressed air from cylinder 64 pushes the solvent from metering loop 34 into the filtration chamber, using a small diameter conduit 62 to insure plug flow. Continued injection of gas (air) agitates the resulting solvent/sample slurry to promote extraction of the soluble species into the liquid phase. After extraction for a predetermined period, the cartridge is rotated 180°, and the liquid phase is filtered out of the cartridge, using air pressure to assist the filtration step. An aliquot of the liquid phase is then captured in metering loop 92 of sample valve 78, and may be injected into conduit 96 for on-line analysis, or may be collected for remote analysis. The undissolved particulate portion of the sample remaining in cartridge 22 is disposed of with the cartridge prior to the succeeding analysis. Yet further details of the invention are illustrated in Examples 1 and 2 below.

EXAMPLE 1

This experiment is used to determine minimum sample agitation (extraction) times using as the sample a dry blended cement powder containing as components of interest: (a) a soluble naphthalene sulfonate polymer; and (b) a commercial grade $CaCl_2$. The experiment uses a cartridge 22 adapted from a 20 cc standard laboratory syringe to which is added a disc filter cut from a ¼" sheet of 10 micron UHMW polyethylene, the sheet being obtained commercially from the Porex Division of Glasrock, Fairburn, Ga. Sample size is 5 grams and solvent volume is 10 ml of a 10% solution of aqueous sodium sulfate, the sulfate being effective to prevent filter plugging as may otherwise be caused by cellulose derivatives in the dry blended cement sample. The metered solvent is added to cartridge 20 through a 0.031" I.D. conduit 62, using an air pressure regulated setting of 20 psi for sample agitation and filtering pressurization. An aliquot of the filtered liquid is collected and injected by sample valve 78 into a carrier fluid of 0.25M $HC_2H_3O_2$ – 0.25M $NaC_2H_3O_2$ in deionized water. Several comparable samples are analyzed with the species (a) of interest determined by UV detection at 254 nm; and the species (b) of interest by a chloride specific electrode. The results of the experiment, summarized in Table I, show that sensitivity in terms of recorded peak height substantially decreases, with increased agitation (extraction) time, indicating thus a decrease in extraction efficiency with extended times of agitation.

TABLE I

EFFECT OF AGITATION TIME ON PEAK HEIGHT
Solvent: 10% $Na_2SO_4$ (aqueous)

| Weight Species (a) (mg) | Weight Species (b) (mg) | Agitation Time (min) | Peak Height Species (a) | Peak Height Species (b) |
|---|---|---|---|---|
| 62.9 | 210 | 4.5 | 21 | 60 |
| 68.2 | 202 | 4.5 | 25 | 46 |
| 63.6 | 202 | 3.0 | 27 | 62 |
| 65.9 | 199 | 3.0 | 27 | 63 |
| 62.4 | 205 | 1.0 | 43 | 54 |
| 65.3 | 202 | 1.0 | 48 | 63 |

EXAMPLE 2

In order to increase extraction efficiency, the solvent is reformulated to include additionally 5% isopropyl alcohol. The alcohol component is believed to improve extraction by lessening surface adsorption effects. The results of this experiment, otherwise comparable to Example 1, are summarized in Table II.

TABLE II

EFFECT OF AGITATION TIME ON PEAK HEIGHT
Solvent: 10% Na$_2$SO$_4$ in 5% v/v 2-Propanol

| Weight Species (a) (mg) | Weight Species (b) (mg) | Agitation Time (min) | Peak Height Species (a) | Peak Height Species (b) |
|---|---|---|---|---|
| 62.4 | 217 | 5.0 | 56 | 57 |
| 61.9 | 197 | 5.0 | 52 | 53 |
| 62.2 | 202 | 3.0 | 48 | 46 |
| 62.5 | 204 | 3.0 | 56 | 48 |
| 62.0 | 205 | 1.0 | 66 | 53 |
| 63.5 | 203 | 1.0 | 66 | 52 |

The data of Table II illustrate substantially lessened criticality of agitation time versus extraction efficiency using a more effective solvent mixture. It is also shown under these conditions that the extraction does not require excessive agitation. For this experiment an agitation time of about 1 minute appears most preferred for the effective extraction of the given solubles of interest from the dry blended cement samples analyzed.

What is claimed is:

1. Method for the batch preparation of sample aliquots by solvent extraction and separation of soluble species from sample comprising nonsoluble particulate, which comprises:
   (a) adding a batch quantity of said sample to a receptacle having a sample receiving space which communicates with a fluid-permeable filter, the filter being disposed remotely from the sample;
   (b) adding a batch quantity of liquid solvent to the sample receiving space;
   (c) injecting a stream of pressurized gas into the sample receiving space to slurry the solvent with the sample;
   (d) inverting the sample receptacle to transfer the slurry into filtering contact with the filter;
   (e) filtering the liquid phase of the slurry through the filter, and
   (f) collecting a metered amount of the filtered liquid phase to prepare a sample aliquot containing dissolved species extracted from the sample.
2. The method of claim 1, wherein the solvent is added to the sample receiving space by the addition of a metered quantity of solvent to said stream of pressurized gas.
3. The method of claim 2, wherein step (e) includes using positive gas pressure in the sample receiving space to pneumatically assist the filtration of the liquid phase of the slurry.

* * * * *